United States Patent [19]
Chandler

[11] Patent Number: 6,139,800
[45] Date of Patent: Oct. 31, 2000

[54] INTERLACED LASERS FOR MULTIPLE FLUORESCENCE MEASUREMENT

[75] Inventor: Van S. Chandler, Austin, Tex.

[73] Assignee: Luminex Corporation, Austin, Tex.

[21] Appl. No.: 09/102,034

[22] Filed: Jun. 22, 1998

Related U.S. Application Data

[60] Provisional application No. 60/050,494, Jun. 23, 1997, and provisional application No. 60/085,381, May 14, 1998.

[51] Int. Cl.$^7$ .................................................. G01N 21/64
[52] U.S. Cl. ........................................ 422/82.08; 356/72
[58] Field of Search ........................... 422/82.08; 436/63, 436/172; 356/72, 73

[56] References Cited

U.S. PATENT DOCUMENTS

| | | | |
|---|---|---|---|
| 4,284,412 | 8/1981 | Hansen et al. | 23/230 |
| 4,745,285 | 5/1988 | Recktenwald et al. | 250/458.1 |
| 5,260,029 | 11/1993 | Hosoi et al. | 422/82.08 |
| 5,569,587 | 10/1996 | Waggoner | 435/6 |
| 5,747,349 | 5/1998 | Van den Engh et al. | 436/172 |

*Primary Examiner*—Jeffrey Snay
*Attorney, Agent, or Firm*—Gilberto M. Villacorta; Pepper Hamilton LLP

[57] ABSTRACT

An apparatus for detecting at least one receptor in a biological sample in a flow stream for immunoassays, complex genetic analyses, and enzymatic assays. The biological sample includes a carrier having an indicator, such as a fluorescent dye, and a reactant that reacts to the receptor. The indicator indicates a presence of the receptor upon excitation by light having a wavelength or a band of wavelengths. The apparatus includes a viewing chamber for receiving the biological sample in the flow stream and for displaying the same. Light sources are arranged around the viewing chamber so as to emit light sequentially, simultaneously, or substantially simultaneously toward substantially identical or overlapping focal regions in the viewing chamber. At least one optical detector is configured to detect light emitted from the sample responsive to light emitted from the light sources. The apparatus includes band-pass filters for filtering out the emission wavelength reflecting the presence of the receptor and at least one multi-mode fiber optic cable connecting the optical detector to the filters.

22 Claims, 10 Drawing Sheets

INTERLACED LASERS FOR MULTIPLE FLUORESCENCE MEASUREMENT

RELATED APPLICATIONS

This application claims priority to U.S. Provisional Application Ser. No. 60/050,494 filed Jun. 23, 1997 and U.S. Provisional Application Ser. No. 60/085,381 filed May 14, 1998, both incorporated herein by reference.

FIELD OF THE INVENTION

The invention relates generally to small particle measurement systems and/or methods, and more particularly, to flow cytometric systems and/or methods of fluorescence measurement, including, multiple fluorescence measurement.

BACKGROUND OF THE INVENTION

Flow cytometry is a method of ascertaining components or structural features of cells or other particles, typically by optical means.

Conventional flow cytometers have been commercially available since the early 1970s and presently cost, for example, more than $120,000. They can be behemoths in size, occupying upwards of 13 cubic feet and weighing well over 200 pounds.

Figure 1:
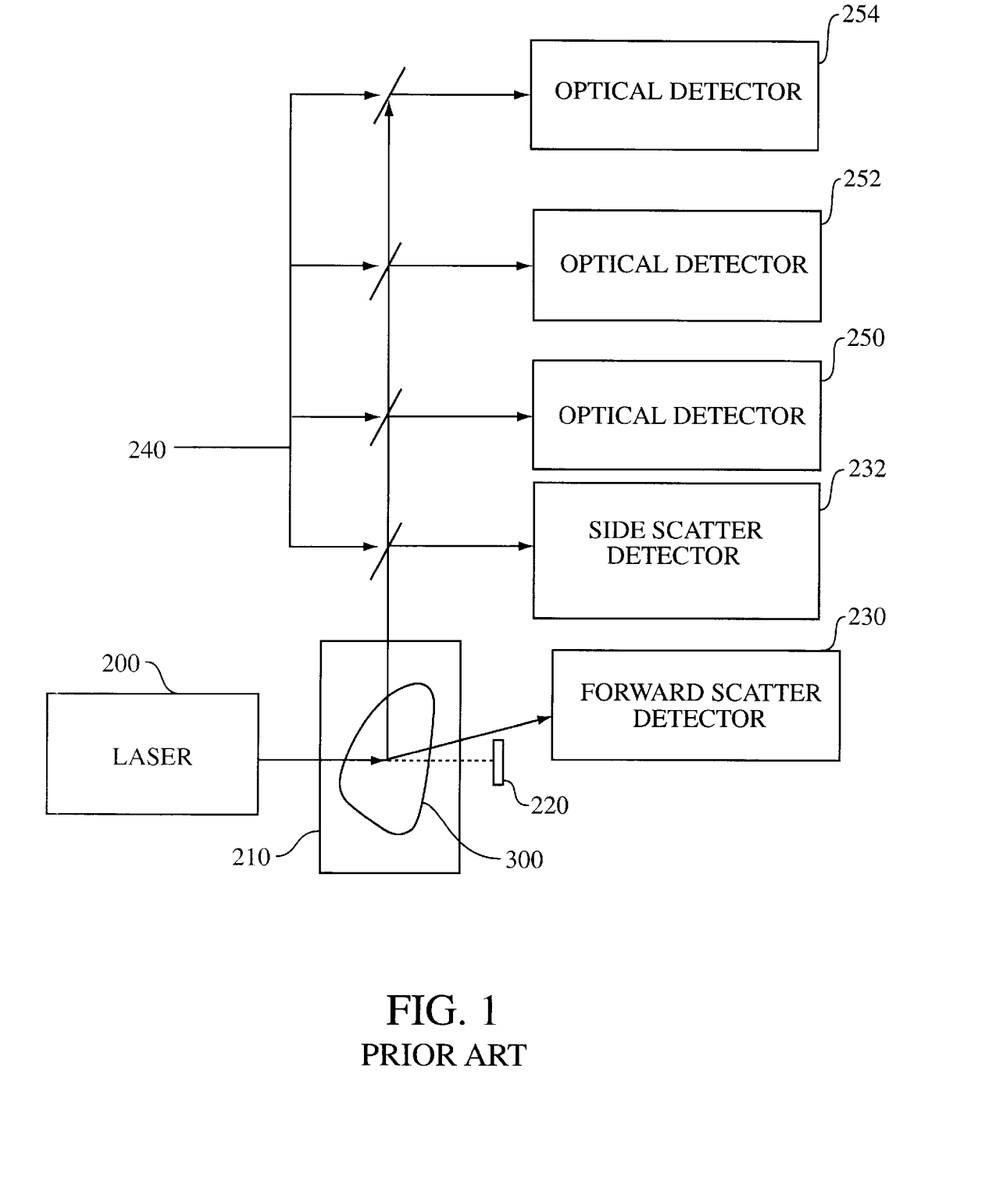
FIG. 1 is a schematic of a prior art flow cytometer.
Figure 2:
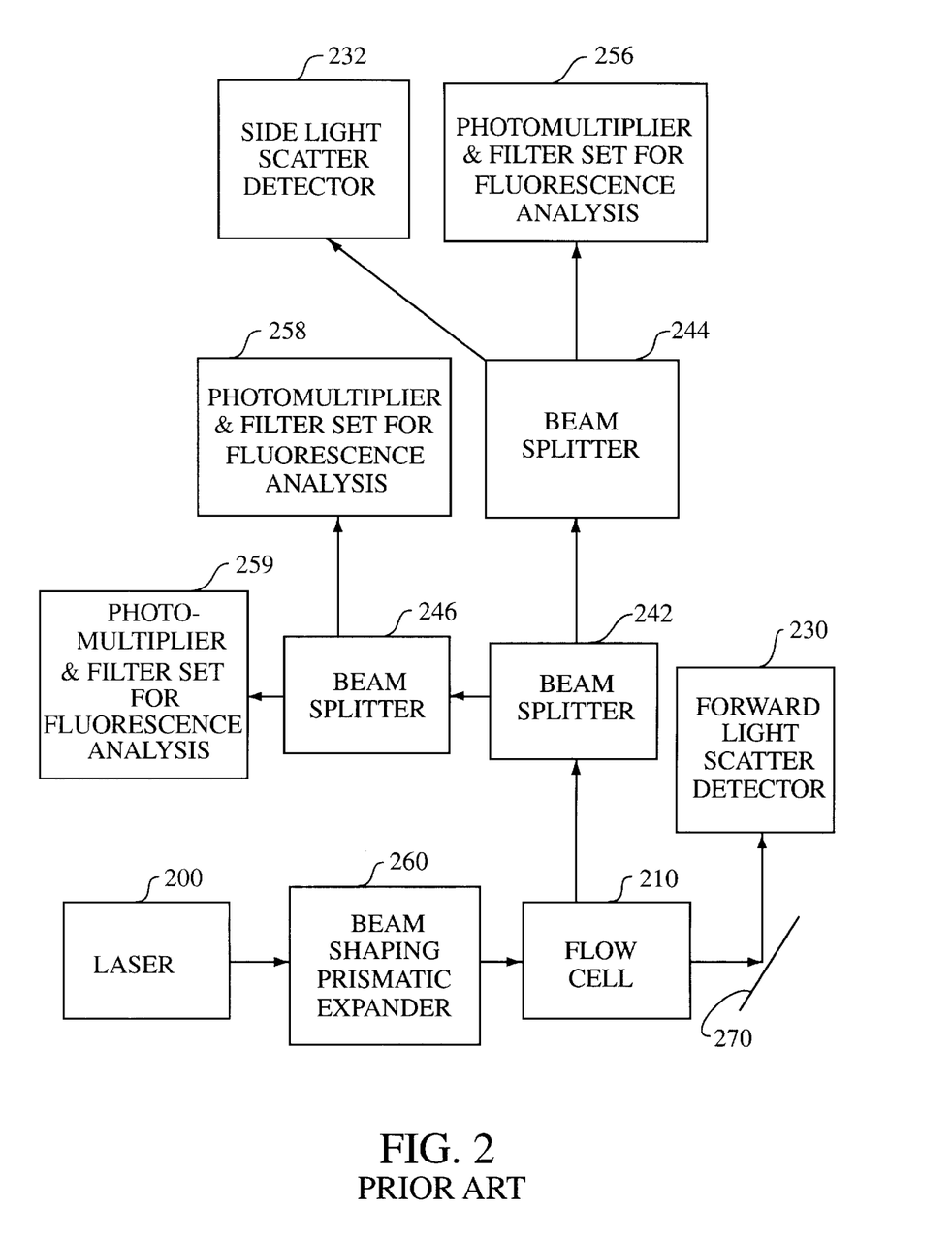
FIG. 2 is a schematic of another prior art flow cytometer.

In conventional flow cytometers, as shown in FIGS. 1 and 2, sample fluid containing sample cells or microspheres having reactants on their surfaces is introduced from a sample tube into the center of a stream of sheath fluid. The sheath fluid is pumped much more quickly than the sample so that the cells or microspheres are constrained to the center of the sheath fluid. This process, known as hydrodynamic focusing, allows the cells to be delivered reproducibly to the center of the measuring point. Typically, the cells or microspheres are in single unit suspension in the flow cell.

A continuous wave laser 200 focuses a laser beam on them as they pass single-file through the laser beam by a continuous flow of a fine stream of the suspension. Lasers in conventional flow cytometers may require shaping a round beam into an elliptical beam to be focussed on the flow cell. As shown in FIG. 2, this elliptical beam may be formed from the round beam using a beam shaping prismatic expander 260 located between the laser and the flow cell.

When the objects of interest in the flow stream are struck by the laser beam, certain signals are picked up by detectors. These signals include forward light scatter intensity and side light scatter intensity. In the flow cytometers, as shown in FIGS. 1 and 2, light scatter detectors 230, 232 are usually located opposite the laser (relative to the cell) to measure forward light scatter intensity, and to one side of the laser, aligned with the fluid-flow/laser beam intersection to measure side scatter light intensity.

In front of the forward light scatter detector 230 can be an opaque bar 220 that blocks incident light from the laser. Forward light scatter intensity provides information concerning the size of individual cells, whereas side light scatter intensity provides information regarding the relative granularity of individual cells.

Known flow cytometers, such as disclosed in U.S. Pat. No. 4,284,412 to HANSEN et al., have been used, for example, to automatically identify subclasses of blood cells. The identification was based on antigenic determinants on the cell surface which react to antibodies which fluoresce. The sample is illuminated by a focused coherent light and forward light scatter, right angle light scatter, and fluorescence are detected and used to identify the cells.

As described in U.S. Pat. No. 5,747,349 to VAN DEN ENGH et al., some such flow cytometers use fluorescent microspheres, which are beads impregnated with a fluorescent dye. Surfaces of the microspheres are coated with a tag that is attracted to a receptor on a cell, an antigen, an antibody, or the like in the sample fluid. So, the microspheres, having fluorescent dyes, bind specifically to cellular constituents. Often two or more dyes are used simultaneously, each dye being responsible for detecting a specific condition.

Typically, the dye is excited by the laser beam from a continuous wave laser 200, and then emits light at a longer wavelength. As shown in FIG. 1, dichroic filters 240 split this emitted light and direct it through optical detectors 250, 252, 254 that can be arranged sequentially 90° relative to the laser. The optical detectors 250, 252, 254 measure the intensity of the wavelength passed through a respective filter. The fluorescence intensity is a function of the number of fluorescent beads attached to a cell or aggregated at portions of the sample/sheath fluid.

FIG. 2 depicts a prior art flow cytometer which uses beam splitters 242, 244, 246 to direct light from the flow cell 210 to photo-multiplier and filter sets 256, 258, 259 and to side light scatter detector 232. This flow cytometer employs a mirror 270 to reflect forward light scatter to forward light scatter detector 230.

If a specific wavelength could be separated out by each optical detector, multiple fluorescent dyes theoretically ought to be able to be applied to a single sample of cells or microspheres. However, I have determined that the properties of the fluorescent dyes themselves limit this flow cytometric technique to about three different wavelengths. The difference in energy, and hence wavelength, between an excitation photon and emission photon is known as Stokes shift. Generally, the larger the Stokes shift from the excitation wavelength, the broader and weaker the emission spectra.

At any given excitation wavelength, I have determined that there are often only about two or three commercially available dyes that emit a spectrum of wavelengths narrow enough and sufficiently separated enough that they are individually measurable simultaneously. Consequently, researchers in flow cytometry and other fields may have been limited to roughly three fluorescent labels, namely, for green, yellow-orange, and red light.

The limitation on the number of fluorescent labels necessarily crimps the amount of analysis that can be done on any one sample. Therefore, for meaningful analysis, a larger quantity of sample is required and more runs of the sample through the flow cytometer must be performed. This necessarily increases the time needed to analyze the sample. However, time is often not available in an emergency room environment, for example, where a small blood sample must be screened simultaneously for many diagnostic indicators, including therapeutic and abused drugs, hormones, markers of heart attack and inflammation, and markers of hepatic and renal function. In addition, for efficiency reasons, it is desirable to minimize the testing time to increase the number of tests that may be performed over a predetermined time interval.

Figure 3:
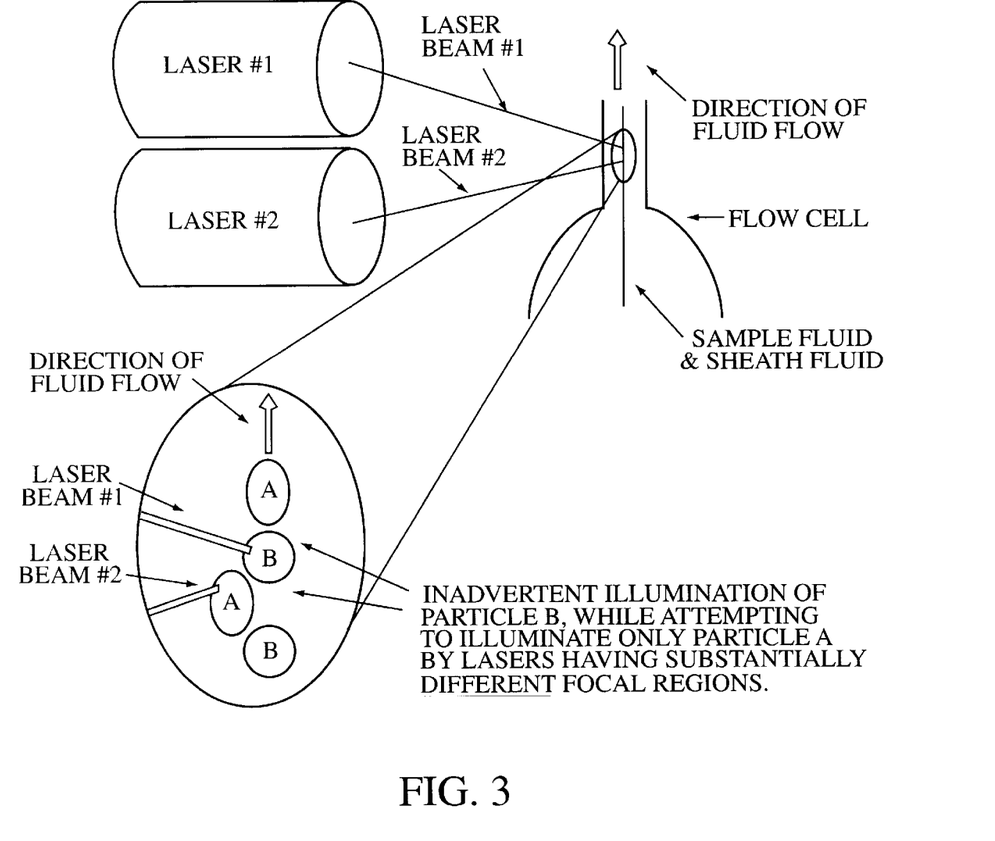
FIG. 3 is a schematic of two lasers in operational relationship with particles traveling through a flow cell.

One way to overcome the limitation on the number of fluorescent labels would be to use two lasers of different frequencies, each focused on a different spot along the flow stream. As a particle passes a first laser, up to three fluorescence measurements could be taken. Then, as the particle passes the second laser, theoretically, up to three more measurements could be taken. FIG. 3 illustrates this method.

It should be noted that the upper pair of particles A, B show the lower pair of particles A, B at a later time as the particles progress upward through the flow cell; the particles themselves are the same. In this case, laser #1 strikes particle A. Laser #2 must wait to emit its beam until it is believed that the same particle A is in range. Only then can the laser #2 emit its beam to strike particle A.

However, despite the intuitive simplicity of this dual laser approach, I have determined that it is often impossible to know for certain whether the measurements are made on the same particle. Because the measurement events at the sets of detectors are separated temporally and spatially, I have discovered that, besides laser emission timing problems, even the slightest flow turbulence can mix particles in suspension, thereby increasing the likelihood that subsequent measurements are not made on the same particle as the previous measurements.

For example, referring to FIG. 3, flow turbulence may cause particle B to change places with particle A such that laser #2 strikes particle B, instead of particle A. By extension, this unacceptable problem compounds as lasers and detectors are added to the device.

In view of this problem, I have determined that it would be desirable to have a system and/or a method for exciting a sample particle at multiple wavelengths in substantially the same time and space domain.

I have further determined that it would be desirable to extend such a system and such a method to a multitude of excitation wavelengths at no significant and/or measurable cost to measurement accuracy.

I have also determined that it would be desirable to have a system and/or a method for measuring multiple fluorescence wavelengths substantially simultaneously that is small and inexpensive relative to conventional flow cytometers.

SUMMARY OF THE INVENTION

It is a therefore feature and an advantage of the instant invention to provide a means/system of, and a method for, exciting a sample particle at multiple wavelengths at substantially the same time and/or space domain.

It is an additional feature and an advantage of the instant invention to extend such a means/system and such a method to a multitude of excitation wavelengths at no substantial cost or effect to measurement accuracy. Consequently, it is another feature and an advantage to perform more assays or measurement per quantity of sample using the instant invention, thereby acquiring more information using a smaller quantity of the sample than using conventional flow cytometers.

It is also a feature and an advantage of the instant invention to provide a means for measuring multiple fluorescence wavelengths that is small and inexpensive relative to conventional flow cytometers.

To achieve the above features and advantages of the invention, an improved apparatus for measuring multiple fluorescence emissions in, for example, flow cytometry and liquid labeling fields is provided. The apparatus includes a viewing chamber. The apparatus also includes a plurality of light sources, where each light source has a substantially identical focal region in the viewing chamber. The apparatus also includes a plurality of optical detectors. Each optical detector is adjacent to, near, or in responsive location with a respective light source of the plurality of light sources.

The apparatus further optionally includes a plurality of filter sets. Each filter set is connected to a respective optical detector. Each filter set optionally includes at least one band-pass filter. The apparatus also optionally comprises a plurality of multi-mode cables. Each multi-mode cable connects each filter set to the respective optical detector. Each band-pass filter can be coupled to a respective amplifying photo-detector. Each amplifying photo-detector, for example, includes a photo-multiplier tube or an avalanche photo-diode.

The apparatus also optionally has a plurality of analog-to-digital converters, where each amplifying photo-detector is connected to a respective analog-to-digital converter. A digital signal processor is optionally connected to the plurality of analog-to-digital converters. A selector is optionally connected to the plurality of analog-to-digital converters and the digital signal processor.

The apparatus, alternatively, further comprises a plurality of multiplexers. Each multiplexer includes inputs connected to each bandpass filter of a respective filter set. A plurality of amplifying photo-detectors is optionally provided. The multiplexer includes an output connected to a respective amplifying photo-detector. Optionally, a plurality of analog-to-digital converters is provided. Each respective amplifying photo-detector is connected to a respective analog-to-digital converter. The apparatus also optionally includes a digital signal processor connected to the plurality of analog-to-digital converters.

The plurality of light sources optionally includes a plurality of optical amplifiers. The plurality of optical amplifiers may include a laser diode and/or a gas laser. The plurality of multi-mode cables may include a plurality of multi-mode fiber optic cables.

The viewing chamber optionally is comprised of a quartz cuvette having a flat air-to-glass interface. The plurality of light sources and the plurality of optical detectors optionally is circumferentially and perpendicularly arranged relative to the viewing chamber in the same plane. Alternatively, the light sources and/or detectors are arranged in different planes, non-perpendicularly, and/or non-circumferentially.

In another embodiment of the invention, an apparatus or system for measuring multiple fluorescence emissions in, for example, flow cytometry and liquid labeling is provided. The apparatus comprises an optional viewing chamber. The apparatus may further comprise a plurality of light sources, where each light source has a substantially identical focal region in the viewing chamber. An optical detector is optionally provided for cooperating with the plurality of light sources.

The apparatus further optionally comprises a plurality of band-pass filters. The apparatus may also comprise a multi-mode fiber optic cable including at least an equal number of bundles as a number of the plurality of band-pass filters. The multi-mode fiber optic cable connects the optical detector to the plurality of band-pass filters.

The apparatus further optionally comprises a multiplexer including inputs connected to the plurality of band-pass filters. A photo-detector may be provided, where the multiplexer includes an output connected to the photo-detector. An analog-to-digital converter is optionally connected to the photo-detector. A digital signal processor may be connected to the analog-to-digital converter.

In another embodiment of the invention, an improved method of measuring multiple fluorescence emissions in, for example, flow cytometry and liquid labeling is provided. The method comprises the following sequential, non-sequential or independent steps. A sample is illuminated in a viewing chamber having a plurality of light sources and a plurality of optical detectors arranged around the viewing chamber. Each light source has a substantially identical focal region relative to remaining light sources. Fluorescence emissions from the sample are measured.

The step of illuminating the sample, optionally further includes illuminating the sample for a period of time using a first light source of the plurality of light sources. The step of measuring fluorescent emissions includes the following sequential, non-sequential or independent steps. The illuminated sample is detected during the period of time using a respective optical amplifier for the first light source. Dark current is detected after the period of time using the respective optical detector. The step of illuminating the sample through detecting dark current is repeated for each remaining optical light source.

According to the inventive method, the plurality of light sources may include an optical amplifier. The plurality of optical amplifiers optionally include, for example, at least one of a laser diode and a gas laser. The method may further comprise the step of measuring a plurality of fluorescence wavelengths by each optical detector.

The step of measuring a plurality of fluorescence wavelengths may include the following sequential, non-sequential or independent steps. Each optical detector is coupled to a respective multi-mode fiber optic cable to create a plurality of signals identical to a signal detected by each optical detector. The signals are filtered using respective band-pass filters. The filtered plurality of signals is amplified using respective photo-detectors. The respective photo-detectors optionally includes, for example, photo-multiplier tubes or avalanche photo-diodes. The amplified plurality of signals is digitized.

The method optionally further comprises the step of reporting a fluorescence level of each digitized signal using a digital signal processor. The step of reporting a fluorescence level may include the following sequential, non-sequential or independent steps. A waveform for the each digitized signal is built using the digital signal processor. Fluorescence levels for the each digitized signal are determined by using, for example, peak detection or integration using the digital signal processor.

The step of measuring a plurality of fluorescence wavelengths can alternatively include the following sequential, non-sequential or independent steps. Each optical detector is coupled to a respective multi-mode fiber optic cable to create a plurality of signals identical to a signal detected by the optical detector. The plurality of signals is filtered using respective band-pass filters. The filtered plurality of signals is multiplexed using a multiplexer. The multiplexed signals are amplified using a photo-detector. The amplified signals are digitized using an analog-to-digital converter.

The present invention is applicable to fields other than flow cytometry, where particles are, for example, irradiated with light for detection and/or analysis purposes.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BEST MODE FOR CARRYING OUT THE INVENTION

Figure 4:
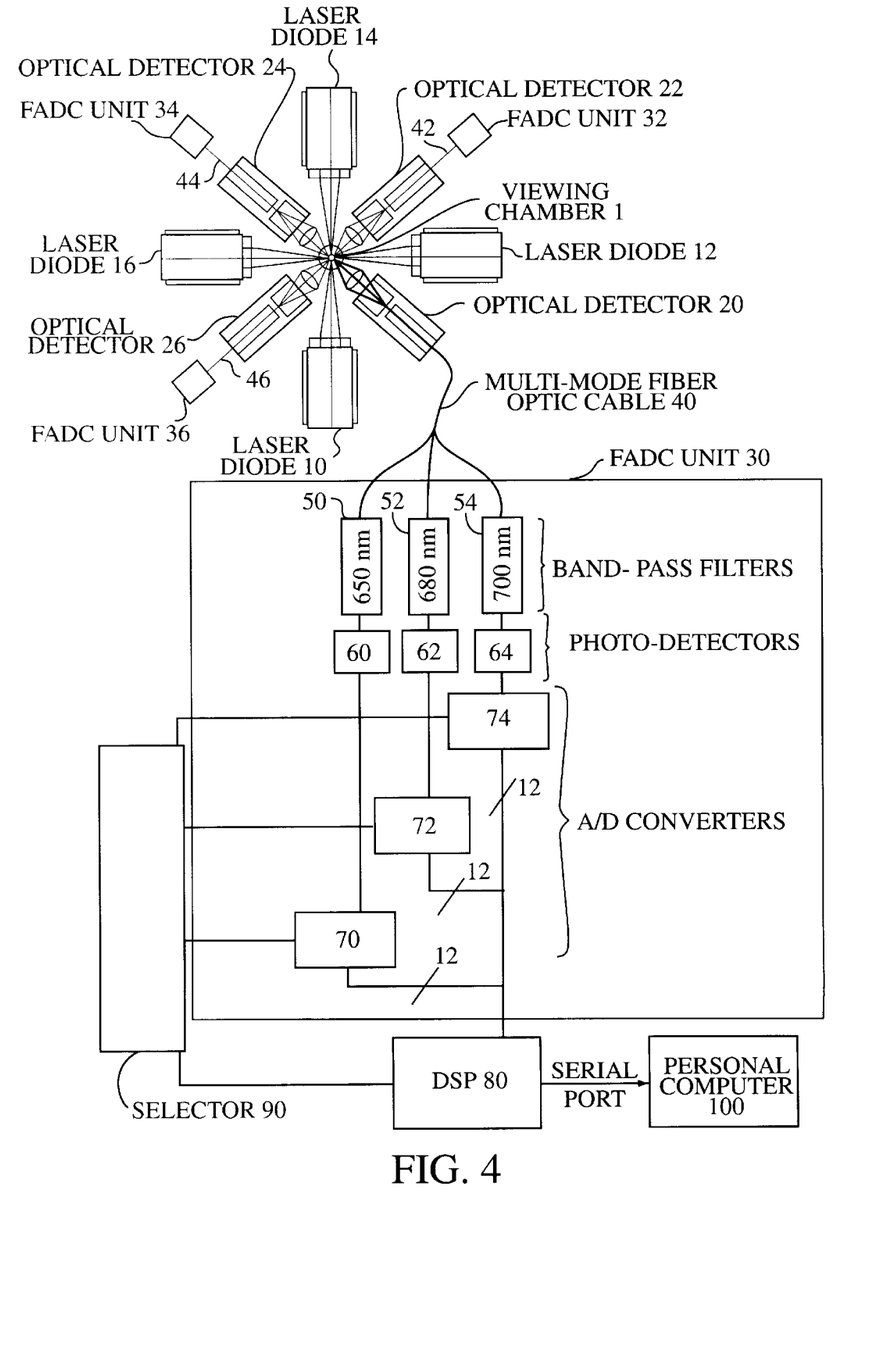
FIG. 4 is a schematic of an embodiment according to the present invention.
Figure 5:
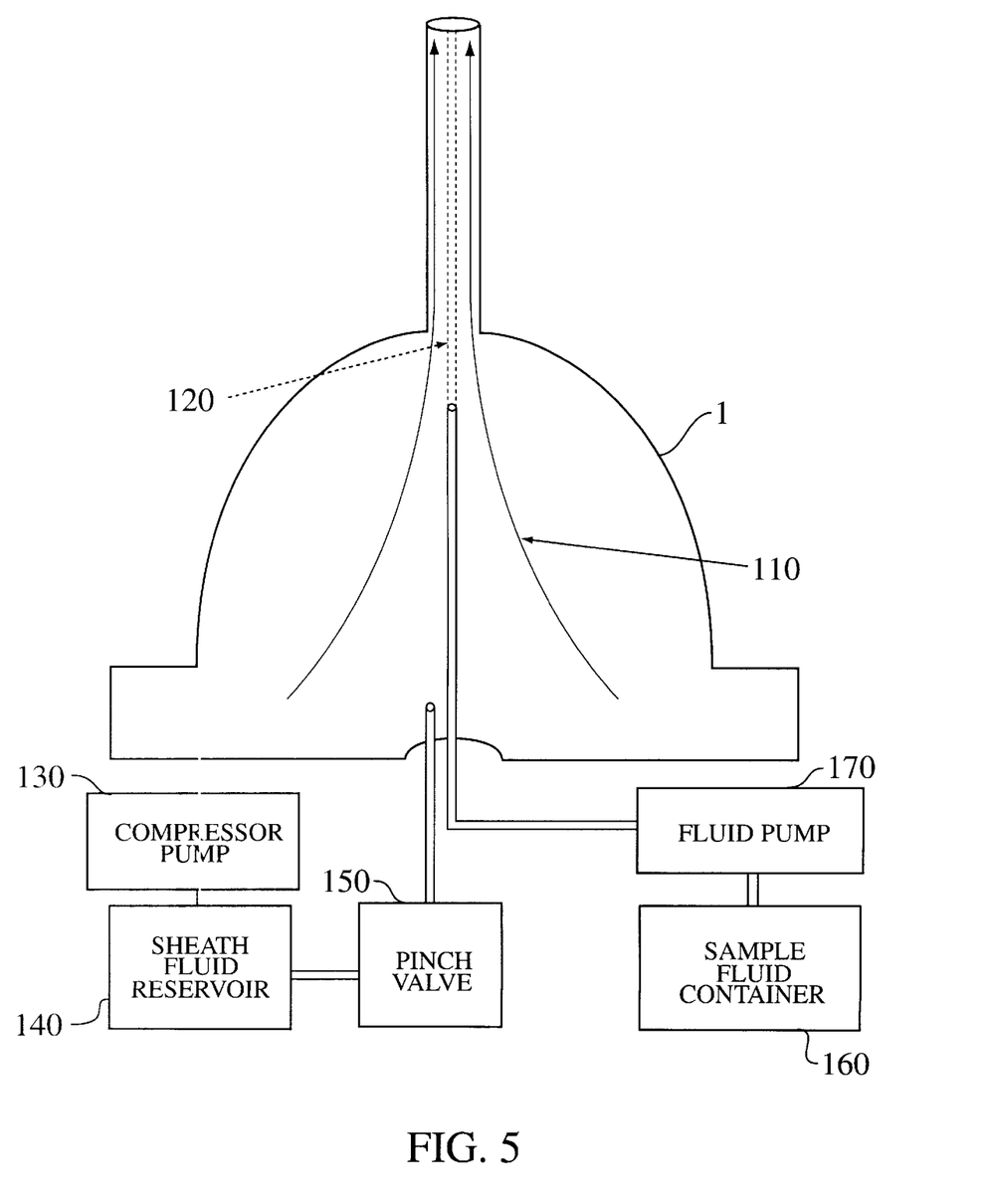
FIG. 5 is a schematic of a cuvette in one optional operation of the instant invention.

FIGS. 4 through 7 show features of a first embodiment of the instant invention. Referring to FIG. 4, the improved flow cytometer includes a sample delivery viewing chamber 1. The viewing chamber 1 can, for example, be a standard quartz cuvette used in standard flow cytometers, as shown in FIGS. 5 and as described below in detail. Of course, other types of viewing or delivery chambers may also be used to deliver the sample for analysis.

According to FIG. 4, four standard laser diodes, or light emitting sources, 10, 12, 14, 16 and four standard optical detectors 20, 22, 24, 26 can surround the periphery of the viewing chamber 1. While FIG. 4 illustrates the use of four optical sources/detectors, any number of optical sources/detectors may be used. Further, while laser diodes have been used in FIG. 4 as the light sources, any suitable light source may be used which is capable of radiating the sample in the cuvette for detection by one or more optical detectors.

By way of illustration, the respective excitation wavelengths of the laser diodes 10, 12, 14, 16 are 633 nm, 670 nm, 710 nm, and 780 nm, respectively. All of the laser diodes 10, 12, 14, 16 share substantially identical, similar, or overlapping focal regions in the viewing chamber 1. For example, all of the laser diodes 10, 12, 14, 16 are optionally focused on a spot 200 microns wide, which may, for example, correspond to the width of the viewing chamber 1, and 140 microns along the length of the stream of flow. Focal spots of other sizes may also be used, for example, larger or smaller than the width of the viewing chamber. Beams of the laser diodes 10, 12 are optionally optically linear in the 200 micron direction and Gaussian in the 140 micron direction. Other beam shapes may be advantageously used as well.

Each optical detector can be associated with an adjacent, near, or operationally responsive laser diode. Optical detector 20 detects emissions resulting from excitation by, for example, laser diode 10; optical detector 22 detects emissions resulting from excitation by, for example, laser diode 12, and the like. Other positional relationships may be used, where multiple overlapping light beams may be radiated sequentially, simultaneously, or substantially simultaneously, regardless of the number of the number of light sources and/or optical detectors.

The optical detectors 20, 22, 24, 26 are connected to respective filtering, amplification, and digital conversion (FADC) units 30, 32, 34, 36 via respective multi-mode fiber optic cables 40, 42, 44, 46. The filtering, amplification, and digital conversion elements of the FADC units, described below, are all standard components. For clarity, components of only FADC unit 30, associated with optical detector 20 and laser diode 10, are shown in FIG. 4. However, it should be understood that each of the remaining FADC units 32, 34, 36, shown in block form, has a comparable configuration to that of FADC unit 30.

Each FADC unit 30, 32, 34, 36 has a respective set of standard band-pass filters 50, 52, 54, a set of standard photo-detectors 60, 62, 64, and a set of standard analog to digital converters (A/D converters) 70, 72, 74. Because the set of band-pass filters in the embodiment shown in FIG. 4 has three band-pass filters 50, 52, 54, the multi-mode fiber 40 correspondingly includes, for example, three bundles, each bundle operatively and/or optically connected to a respective band-pass filter.

In the embodiment shown in FIG. 4, there are four multi-mode fiber optic cables 40, 42, 44, 46, each connected to a corresponding optical detector; each of the four sets of three band-pass filters are connected to each of the four multi-mode fiber optic cables. Alternatively, more multi-mode fiber optic cables than band-pass filter sets are acceptable. Or, more bundles per multi-mode fiber optic cable than band-pass filters per filter set are also acceptable. Either alternative permits upgrading the apparatus to accommodate more band-pass filters as the variety of suitable fluorescent dyes or other acceptable indicators increases.

Although FIG. 4 depicts a separate multi-mode cable for each filter set, a single multi-mode cable may also be used where the various signals are multiplexed. In addition, any suitable transmission medium may be used to transmit the detected signals for analysis. That is, fiber optic cables 40, 42, 44, 46 are described here for illustration purposes, and not by way of limitation.

The band-pass filters 50, 52, 54 remove the excitation wavelength of a respective laser diode to allow the emission wavelength of a fluorescent dye to be seen or measured. A given band-pass filter is substantially centered so as to correspond to the emission wavelength, or band of wavelengths, of an available fluorescent dye associated with an excitation wavelength of a particular laser diode. By way of example, the three band-pass filters 50, 52, 54, associated with the laser diode 10 having an excitation wavelength of 633 nm, are substantially centered at 650 nm, 680 nm, and 700 nm, respectively.

Naturally, these particular band-pass wavelengths are only representative of all possible emission wavelengths of available dyes that fluoresce given an excitation wavelength of 633 nm. Similarly, by way of example, the three band-pass filters, associated with the laser diode 12 having an excitation wavelength of 670 nm, are substantially centered at 680 nm, 690nm, and 700 nm, respectively.

Other lasers, optical sources, detectors, and/or filters may be used having different wavelengths, so long as the different wavelengths are sufficiently spaced for detection and filtering operations, and have a detectable effect on the dye. Similarly, other standard dyes may also be used that provide the ability to detect the desired characteristics.

Each of the band-pass filters 50, 52, 54 are optionally connected to a respective photo-detector 60, 62, 64. The photo-detectors 60, 62, 64 are, for example, photo-multiplier tubes and/or avalanche photo-diodes. Each such photo-detector optionally amplifies a signal transmitted through the corresponding band-pass filter. Each of the photo-detectors 60, 62, 64 are connected to one or more A/D converters 70, 72, 74, all of which in turn are connected to one or more standard digital signal processors 80 (DSP). For purposes of illustration, one DSP 80 is shown.

A standard selector 90 is optionally connected to each of the A/D converters 70, 72, 74, as well as the DSP 80. The selector 90 is used to select which of the A/D converters 70, 72, 74 can transfer its data to one or more DSPs 80 at a given time. The DSP 80 can be connected to a standard serial port, for example, of a standard personal computer 100. It is possible that with multiple DSPs 80, data transfer may be conducted through a standard common bus, which connects the multiple DSPs and to a standard parallel port, for example, of the computer 100.

Figure 6:
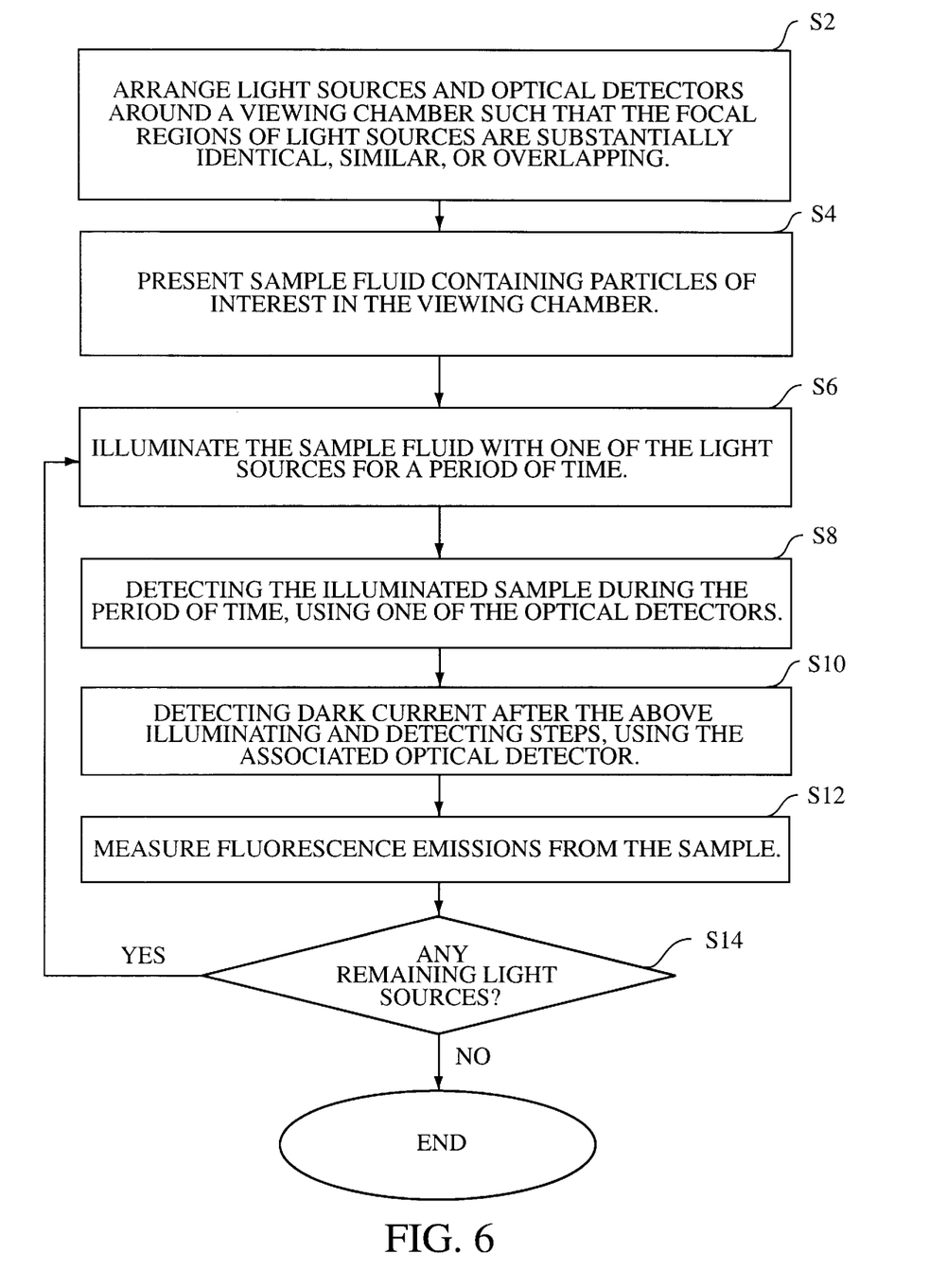
FIG. 6 is a flow chart for one optional operation of the instant invention.

Referring to FIGS. 5 and 6, the method of operation of the instant invention is, for example, as follows:

As indicated at step S2 in FIG. 6, light sources and optical detectors are arranged around a viewing chamber such that the focal regions are substantially identical, similar, or overlapping. More concretely, by way of illustration, laser diodes 10, 12, 14, 16 and optical detectors 20, 22, 24, 26, are arranged around the cuvette 1 such that the focal regions of the laser diodes are substantially identical, similar, or overlapping.

According to step S4, sample fluid 120 containing particles of interest are presented in the viewing chamber. By way of non-limiting example and explanation, a standard compressor pump 130 optionally provides air or gas pressure of approximately 5.5 psi, for example, over the top of a body of sheath fluid 110 in a sheath fluid reservoir 140, urging the sheath fluid toward and through the cuvette 1.

Sheath fluid pressure is optionally regulated by a pinch valve 150, or other suitable standard regulator. Other standard devices may also be used to supply the air pressure. Further, the sheath fluid 110 itself is any hydro-dynamically acceptable medium, for example, purified water. A conventional fluid pump 170, for example, draws sample fluid 120 containing the cells and fluorescent microspheres out of a sample fluid container 160 and presents a drop of the sample fluid 120 into the flow of the sheath fluid 110 at approximately the neck down region of the cuvette 1.

The fluid pump 170 is, by way of illustration, a syringe pump or an injection needle. The neck down region of the cuvette looks like a bottom half of an hour glass. The cells and microspheres in the sample fluid 120 pass out of the end of the fluid pump 170 and become ensheathed in the sheath fluid 110. The reduced cross-section of the neck down region relative to larger portions of the cuvette 1 causes the sheath fluid 110 to accelerate.

As a result, the confluence of the sample fluid 120 and the sheath fluid 110 form a coaxial, bi-component stream, wherein the sample fluid 120 forms the inner component of the stream. The sheath fluid 110 elongates the sample fluid 120, causing the particles therein to form a substantially single file by the time they reach the shared focal region of the laser diodes 10, 12, 14, 16.

At step S6, the sample fluid 120 is illuminated by one of the light sources for a period of time. More specifically, as a particle enters the focal region, it is illuminated by one of the four laser diodes 10, 12, 14, 16 for example, laser diode 10, for about one microsecond, by way of illustration. Alternatively, more than one of the laser diodes may simultaneously or substantially simultaneously illuminate the sample.

As indicated at step S8, during this period of illumination, the illuminated sample is detected by one of the optical detectors 20, 22, 24, 26. Using the non-limiting example mentioned above, optical detector 20 detects the illuminated sample when laser diode 10 is on. If more than one laser diode is on, then all respective optical detectors optionally detect the illuminated sample.

In step S10, dark current is detected after steps S6 and S8, when the light source which was illuminating the sample has been turned off. By illustration, each such illumination is optionally followed by, for example, about one microsecond of darkness, so that the dark current at optical detector 20 can be measured for the sample. Alternatively, for example, two light sources may be activated substantially simultaneously followed by two other light sources activated substantially simultaneously. Other suitable light emission patterns or combinations may also be used.

By way of explanation, when the laser diode 10 is on, the optical detector 20 gathers photons and can couple or transmit them to a respective multi-mode fiber optic cable 30. The cable 30, divided into three bundles, conveys the photons to the three band-pass filters 40, 42, 44. The output of the filters is optically coupled to the photo-detectors 50, 52, 54. The output of the photo-detectors is selectively passed by the selector 90 through the respective A/D converters 70, 72, 74 to the DSP 80, where it may be stored in circular buffers until the output is processed by the DSP. Other types of buffers are available. Indeed, no buffers are required.

The DSP 80 builds waveforms of each measured emission frequency using conventional software. A particle of interest in the viewing chamber is detected by a number of known ways including, for example, fluorescence thresholds, fundamental frequency light scatter, and optical gates. When the particle has left the focal region, the DSP 80 analyzes the waveforms and reports fluorescence levels via standard peak detection or integration techniques, as may be appropriate for the size of the microspheres used.

Those skilled in the art can perform a variety of standard post-processing algorithms on the waveforms, by way of example, for smoothing them or removing high frequency noise therefrom. These algorithms optionally includes standard finite impulse response (FIR) filters or domain transforms. The output of the DSP 80 is optionally read and stored in the memory of the personal computer 100, or immediately displayed on an optional display. Then, the laser diode 10 is switched off, and the subsequent dark current can be measured by the optical detector 20 and stored in the memory of the personal computer 100. Then, as indicated in step S14 in FIG. 6, this is optionally repeated for each of the remaining laser diodes 12, 14, 16, sequentially, substantially simultaneously, or simultaneously for one or more light sources.

Figure 7:
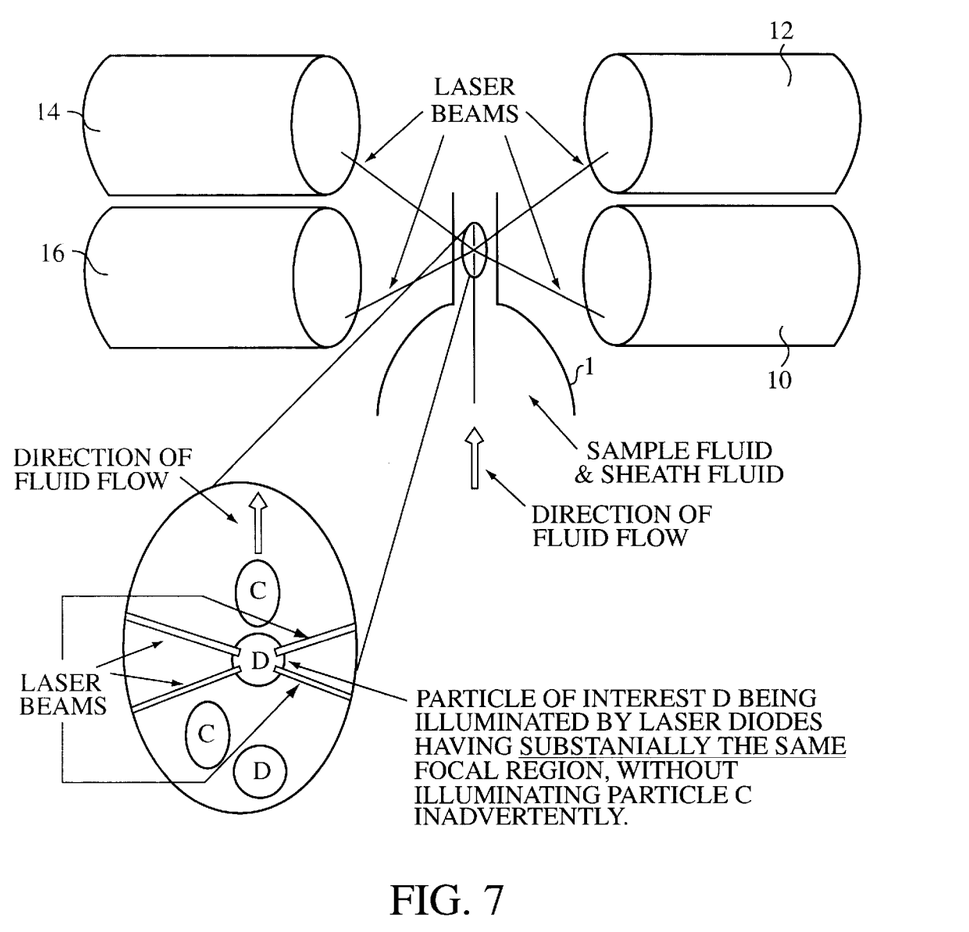
FIG. 7 is a schematic of the instant invention in operational relationship with particles traveling through the viewing chamber.

As illustrated in FIG. 7, all of the laser diodes 10, 12, 14, 16 advantageously have substantially identical, similar, or overlapping focal regions. In this case, the substantially shared focal region is located on particle D for all of the laser diodes 10, 12, 14, 16.

It should be noted that FIG. 7 is not intended to imply that all of the laser diodes 10, 12, 14, 16 are required to illuminate the sample simultaneously. Because of the substantially identical focal region, the existence of particle C advantageously will be less likely to be inadvertently illuminated and/or detected, when attempting to detect particle D. The above-mentioned light sources have been herein described, for illustrative purposes, as having substantially identical, similar, or overlapping focal regions. However, the invention may optionally include light sources having focal regions that are not overlapping, provided that the focal regions are all on the same sample particle.

Alternatively, simultaneous or substantially simultaneous sample illumination is acceptable, provided that adequate differentiation of the detected wavelengths or bands of wavelengths by the FADC units 30, 30' is possible. Indeed, simultaneous or substantially simultaneous illumination of the sample in more than one focal region on the same sample, would also conform to the scope of invention.

Sample fluid 120 and sheath fluid 110, after having passed through the flow cell, are generally discarded through standard biohazard disposal.

Alternative features of the instant invention optionally include the following. Any light source suitable for flow analysis is acceptable. For example, laser diodes having respective excitation frequencies of 414 nm, 710 nm and 780 nm are available and are suitable for use as light sources in the instant invention. Although laser diodes have been described herein, broad spectrum arc lamps, including mercury and xenon arc lamps, standard flash lamps, as well as lasers, including He-Ne, Ar-ion, Ar/Kr, and UV lasers, can optionally be used.

Lasers that can emit light at more than one wavelength simultaneously or substantially simultaneously can also be used. For example, in this regard, there is at least one laser which emits at 488 nm and 357 nm simultaneously. In this situation, one laser would replace two single beam lasers/light sources. Alternatively, frequency tunable lasers are also acceptable. Frequency tunable lasers include, for example, dye lasers, excimer lasers, and semiconductor lasers. Use of a frequency tunable laser may reduce the number of required light sources, and consequently, the number of required optical detectors. Likewise, frequency tunable laser diodes and other frequency tunable light sources are also within the scope of the invention.

The arc lamps may require conventional polarizers in the light path toward the viewing chamber. The lasers may require standard beam shaping prismatic expanders or their equivalents between the light sources and the flow cell. A possible disadvantage to using arc lamps and lasers as well as polarizers and prismatic expanders, is increased size of the overall apparatus relative to an embodiment using laser diodes. Also, the lasers that emit at more than one wavelength often require different prismatic expanders for each wavelength. But, for practical reasons, one set of prismatic expanders may be used for both wavelengths.

A substantially planar light source/optical detector arrangement, wherein the light sources and the optical detectors are substantially circumferentially and substantially perpendicularly arranged relative to a flow direction of the viewing chamber, has only been illustrated and described by way of example. However, other suitable arrangements are available, provided the above-described operative relationships between the one or more light sources and the one or more optical detectors are respected. For example, a non-planar light source/optical detector arrangement is possible. Similarly, a light source/optical detector arrangement, such that the light sources are recessed relative to the optical detectors, or vice versa, are also possible. Further, other non-planar, non-perpendicular and/or non-circumferential arrangements may also be used.

Additionally, any number of light sources 10; 12, 14, 16 and optical detectors 20, 22, 24, 26 are acceptable. Four of each of the light sources and detectors have been shown in FIG. 4 for purposes of illustration only. That is, for example, two, three, five, or more light sources and two, three, five, or more optical detectors also would be keeping in the spirit of the invention.

The optical detectors 20, 22, 24, 26 and the multi-mode fiber optic cable 30 are replaceable with a fewer, an equal, or a larger number of beam splitters, as appropriate. The beam splitters are located between the flow cell and the band-pass filters 50, 52, 54. Those skilled in the art can readily determine appropriately interchanging dichroic optical filters for beam splitters, if an alternative to the beam splitter approach is desired. The beam splitter approach, however, generally increases the size and manufacturing complexity, in contrast to the simpler and/or more compact and/or less expensive optical detector/multi-mode fiber optic cable approach.

Three band-pass filters 50, 52, 54 have been shown for purposes of illustration. However, as few as one or two band-pass filters would be acceptable, and more than three filters may alternatively be used. The maximum number of band-pass filters in a filter set associated with a given light source is determined, for example, by the number of fluorescent dyes that require the excitation wavelength of the given light source and have emission wavelengths that are distinguishable from one another. Alternatively, any number of filters may be used, for example, where several filters are configured in series. Any number of fluorescent dyes or other indicator means may be available for different excitation wavelengths. Consequently, each of the FADC units 30, 32, 34, 36 may have one or a number of different band-pass filters because each unit is associatable with one or more light sources having different excitation wavelengths.

Figure 8:
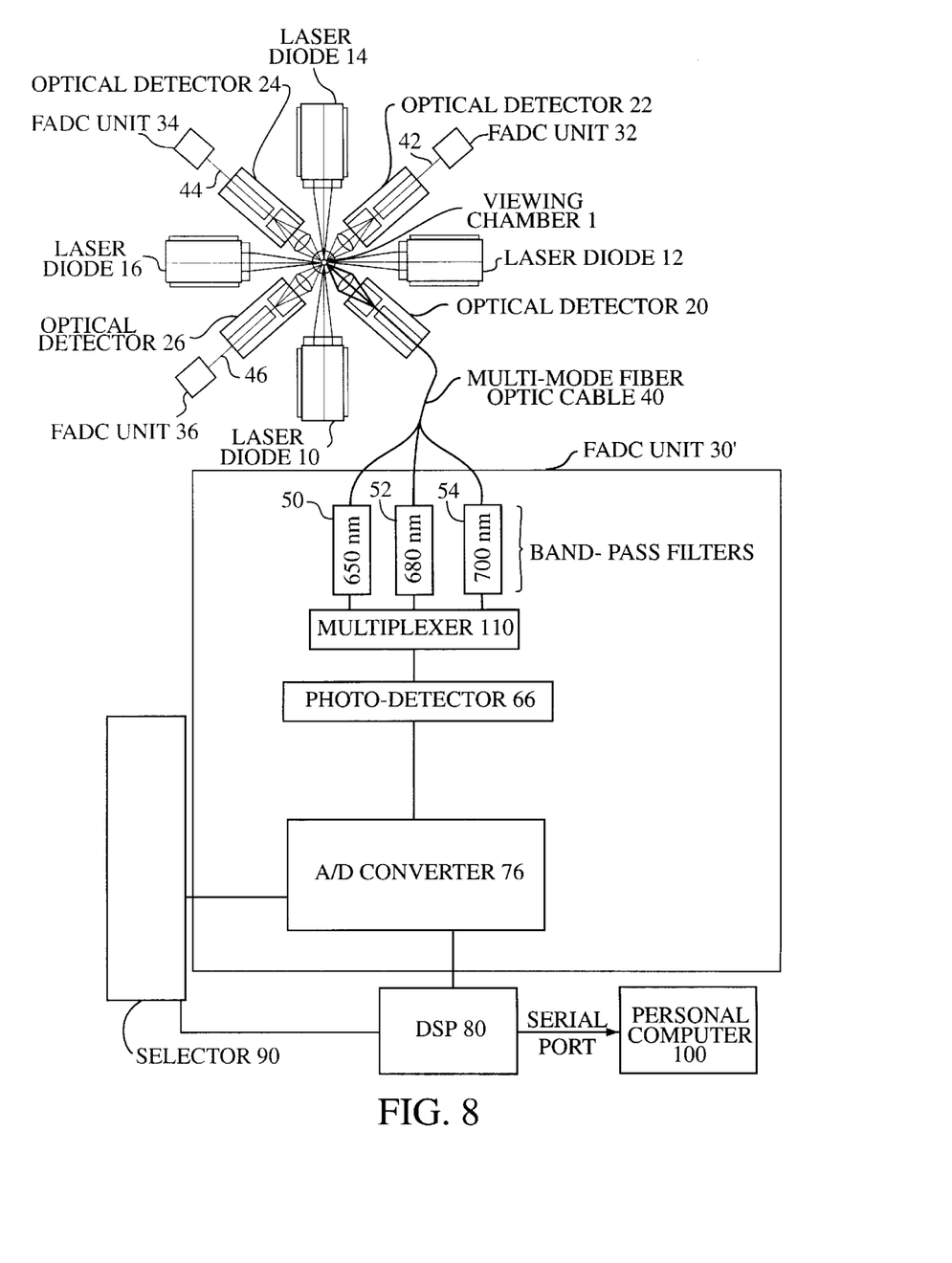
FIG. 8 is a schematic of an alternate embodiment of the present invention.

The number of photo-detectors and A/D converters can be reduced using standard multiplexing techniques known to those skilled in the art. For example, an alternate embodiment of the instant invention with an alternative FADC unit 30' is shown in FIG. 8. Each of the band-pass filters 40, 42, 44 is connectable to a multiplexer 110, which in turn is connectable to a photo-detector 66 and an A/D converter 76. Plainly, an advantage to using such a multiplexing technique would be a reduction in complexity and/or cost of the overall flow cytometer resulting from fewer photo-detectors and fewer A/D converters being needed.

By extension, to further reduce the total cost of the improved flow cytometer, it is possible to eliminate all but one of the optical detectors 20, 22, 24, 26. This embodiment entails connecting the remaining optical detector to all of the band-pass filters via a single multi-mode fiber optic cable having at least as many bundles as there are band-pass filters.

Figure 9:
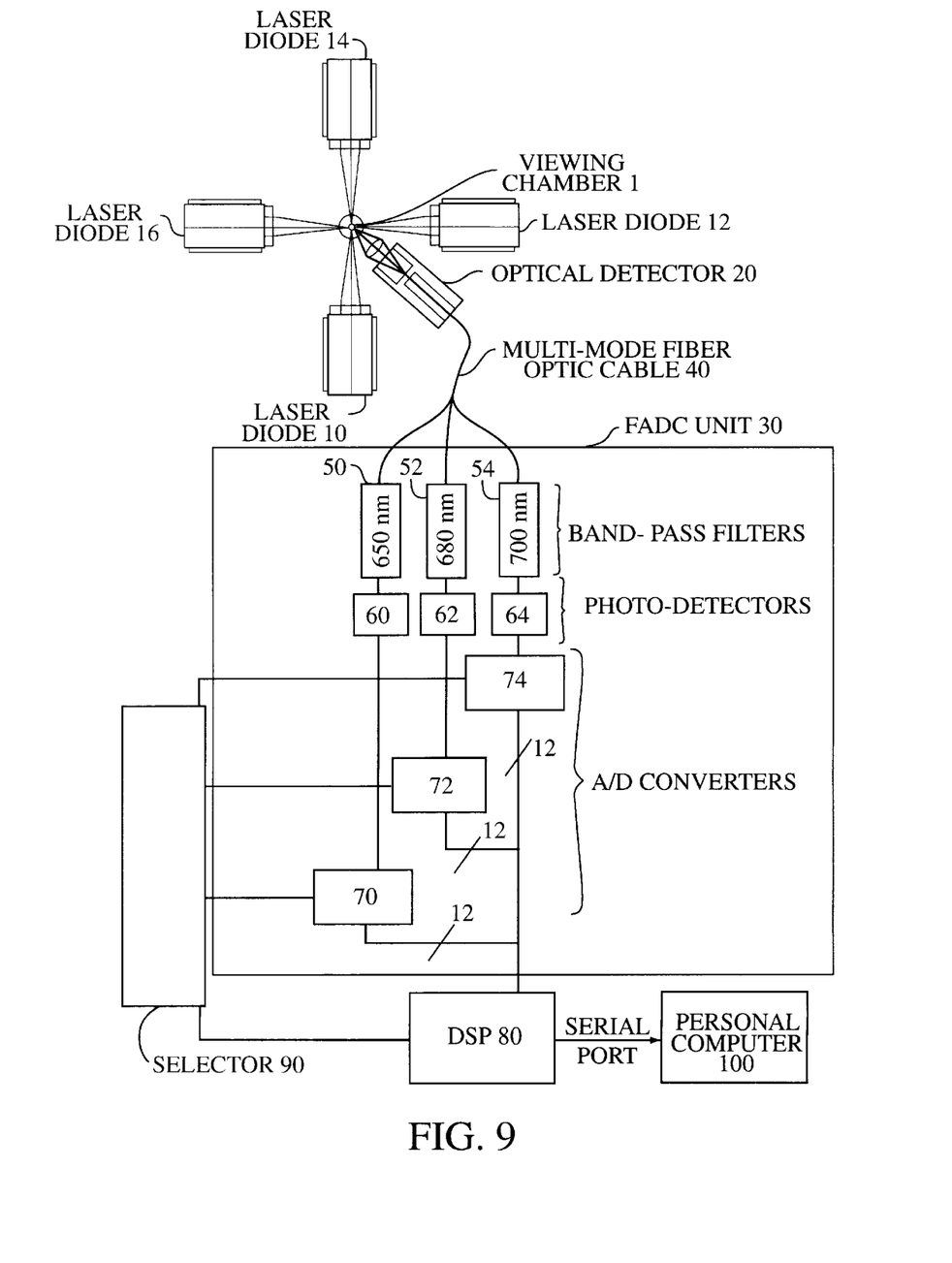
FIG. 9 is a schematic of another alternate embodiment of the present invention.
Figure 10:
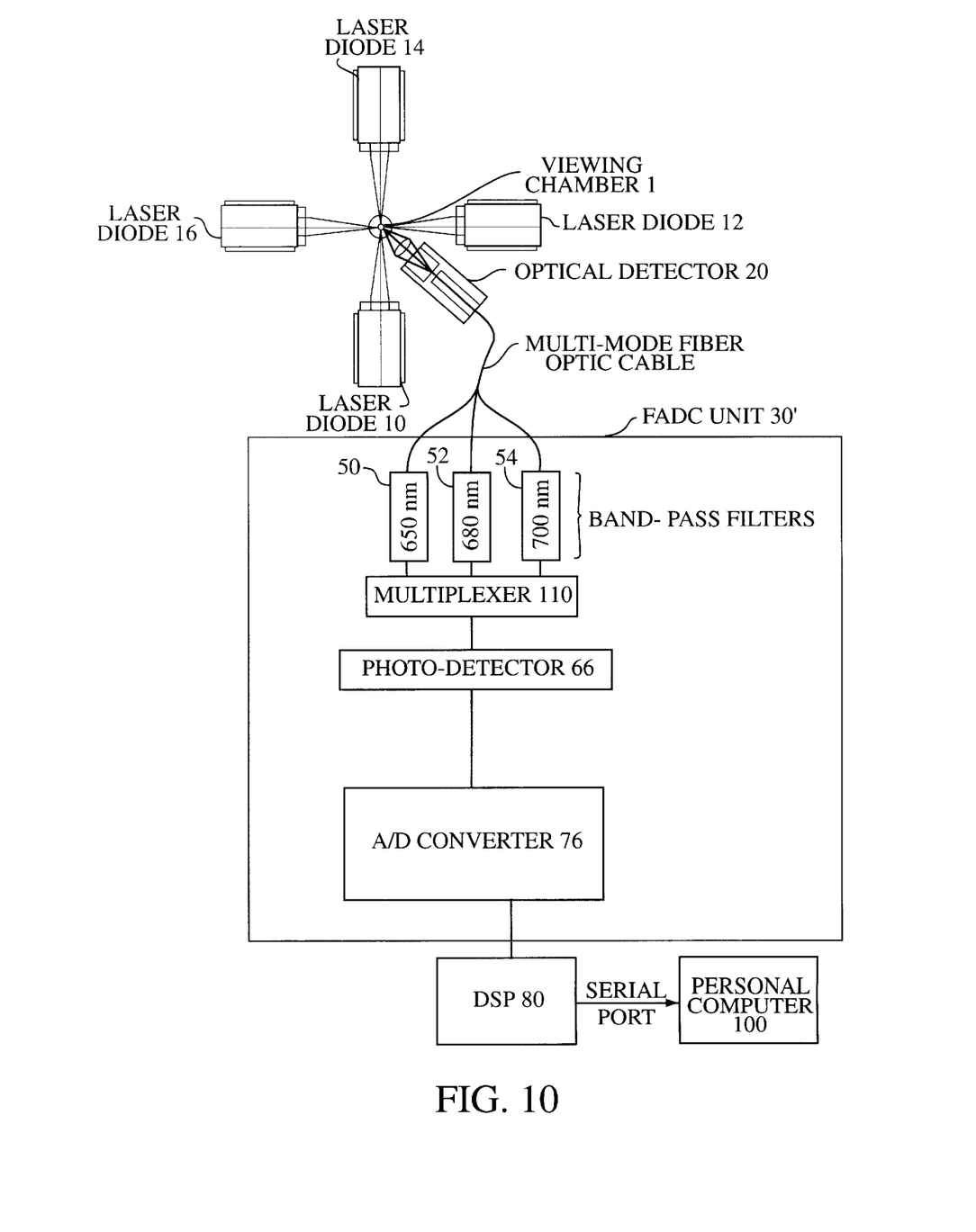
FIG. 10 is a schematic of another alternate embodiment of the present invention.

Two variations of this embodiment are shown in FIGS. 9 and 10. The variation in FIG. 9 has a FADC unit 30, whereas the variation in FIG. 10 has a FADC unit 30' using a multiplexer. Note that the variation in FIG. 10 would not require a selector 90. Because only one analog-to-digital converter 76 is required in the variation according to FIG. 10, a selector for selecting between multiple analog-to-digital converters would not be necessary.

Generally, the relative elements and operations of the variations in FIGS. 9 and 10 are in accordance with the explanations set forth above regarding FIGS. 4 and 8, respectively. However, whereas four optical detectors 20, 22, 24, 26 detect the illuminated sample in FIGS. 4 and 8, one optical detector 20 in the variations of FIGS. 9 and 10 detects the sample illuminated sequentially, simultaneously, or substantially simultaneously by one or more light sources.

In addition, fluorescent dyes and microspheres have been described herein for illustration. However, other suitable light-activated indicators, which can be detected by optical detectors, are available. Likewise, carriers, other than microspheres, capable of carrying both one or more indicators and one or more reactants are suitable for the instant invention.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An apparatus for detecting at least one receptor in at least one biological sample in a flow stream for at least one of immunoassays, complex genetic analyses, and enzymatic assays, the biological sample including at least one indicator indicating a presence of the at least one receptor upon excitation by at least one of a wavelength and band of wavelengths, said apparatus comprising:

a viewing chamber receiving the at least one biological sample and providing a plurality of focal regions therefor;

a plurality of light sources configured to emit light, one of sequentially, simultaneously, and substantially simultaneously, toward a substantially identical focal region of said plurality of focal regions in said viewing chamber on said at least one biological sample; and a plurality of optical detectors in optical relationship with said plurality of light sources, respectively, and detecting a plurality of sample light emitted from said at least one sample responsive to the light emitted from the substantially identical focal region of said at least one biological sample.

2. The apparatus according to claim 1, further comprising:
a plurality of filter sets, each filter set including at least one band-pass filter connected to a respective optical detector, respectively; and
a plurality of multi-mode cables connecting said plurality of filter sets to said plurality of optical detectors, respectively.

3. The apparatus according to claim 2, wherein each band-pass filter is coupled to a respective amplifying photo-detector.

4. The apparatus according to claim 3, wherein each amplifying photo-detector includes one of a photo-multiplier tube and an avalanche photo-diode.

5. The apparatus according to claim 3, further comprising:
a plurality of analog-to-digital converters, said each amplifying photo-detector connected to a respective analog-to-digital converter;
a digital signal processor connected to said plurality of analog-to-digital converters; and
a selector connected to said plurality of analog-to-digital converters and to said digital signal processor.

6. The apparatus according to claim 1, wherein said plurality of light sources includes one of an optical amplifier and an arc lamp.

7. The apparatus according to claim 6, wherein said plurality of optical amplifiers includes at least one of a laser diode and a gas laser.

8. The apparatus according to claim 2, further comprising:
a plurality of multiplexers, each multiplexer including inputs, connected to each band-pass filter of a respective filter set, and outputs;
a plurality of amplifying photo-detectors connected to the outputs of said plurality of multiplexers;
a plurality of analog-to-digital converters connected to said plurality of amplifying photo-detectors;
a digital signal processor connected to said plurality of analog-to-digital converters; and
a selector connected to said digital signal processor and to said plurality of analog-to-digital converters.

9. The apparatus according to claim 2, wherein said plurality of multi-mode cables includes a multi-mode fiber optic cable.

10. The apparatus according to claim 1, wherein said viewing chamber comprises a quartz cuvette.

11. The apparatus according to claim 1, wherein said plurality of light sources and said plurality of optical detectors are substantially circumferentially and substantially perpendicularly arranged relative to a flow direction in said viewing chamber.

12. An apparatus for detecting at least one receptor in at least one biological sample in a flow stream for at least one of immunoassays, complex genetic analyses, and enzymatic assays, the at least one biological sample including at least one indicator indicating a presence of the at least one receptor upon excitation by a wavelength or band of wavelengths, said apparatus comprising:
a viewing chamber receiving the at least one biological sample in the flow stream;
a plurality of light sources, each directed to one of substantially identical and overlapping focal region with respect to said viewing chamber relative to remaining light sources of said plurality of light sources; and
at least one optical detector detecting light at least one of emitted and reflected from the at least one biological sample.

13. The apparatus according to claim 12, further comprising:
a plurality of band-pass filters operatively connected to said at least one optical detector; and
a multi-mode fiber optic cable including a number of bundles at least equal to a number of said plurality of band-pass filters, said multi-mode fiber optic cable connecting said optical detector to said plurality of band-pass filters.

14. The apparatus according to claim 13, further comprising:
a multiplexer including inputs connected to said plurality of band-pass filters;
a photo-detector, said multiplexer including an output connected to said photo-detector;
an analog-to-digital converter connected to said photo-detector; and
a digital signal processor connected to said analog-to-digital converter.

15. The apparatus according to claim 13, further comprising:
a plurality of photo-detectors, each photo-detector connected to a respective band-pass filter;
a plurality of analog-to-digital converters, each analog-to-digital converter connected to a respective photo-detector;
a digital signal processor connected to said plurality of analog-to-digital converters; and
a selector connected to said plurality of analog-to-digital converters and to said digital signal processor.

16. An apparatus for detecting at least two receptors in a biological sample transported in a flow stream for at least one of immunoassays, complex genetic analyses, and enzymatic assays, the biological sample including at least two indicators indicating a presence of the at least two receptors upon excitation by a wavelength or band of wavelengths, said apparatus comprising:
a viewing chamber receiving the biological sample transported via the flow stream;
a plurality of light sources arranged to emit, one of sequentially, simultaneously, and substantially simultaneously, light having at least two focal regions on the biological sample so as to illuminate the biological sample at a same or substantially same location in said viewing chamber, said plurality of light sources having wavelengths or bands of wavelengths selected to excite the at least two indicators in the biological sample by emitting the light on the two focal regions;
at least one optical detector optically responsive to said plurality of light sources so as to detect the presence of the at least two receptors.

17. The apparatus according to claim 16, further comprising:
a plurality of filter sets, each filter set including at least one band-pass filter connected to a respective optical detector, respectively; and
a plurality of multi-mode cables connecting said plurality of filter sets to said plurality of optical detectors, respectively.

18. The apparatus according to claim 17, further comprising:
- a plurality of amplifying photo-detectors, each amplifying photo-detector operatively coupled to a respective band-pass filter;
- a plurality of analog-to-digital converters, said each amplifying photo-detector connected to a respective analog-to-digital converter;
- a digital signal processor connected to said plurality of analog-to-digital converters; and
- a selector connected to said plurality of analog-to-digital converters and to said digital signal processor.

19. The apparatus according to claim 17, further comprising:
- a plurality of multiplexers, each multiplexer including inputs, connected to each band-pass filter of a respective filter set, and outputs;
- a plurality of amplifying photo-detectors connected to the outputs of said plurality of multiplexers;
- a plurality of analog-to-digital converters connected to said plurality of amplifying photo-detectors;
- a digital signal processor connected to said plurality of analog-to-digital converters; and
- a selector connected to said digital signal processor and to said plurality of analog-to-digital converters.

20. The apparatus according to claim 17 wherein the at least two focal regions are one of non-overlapping and overlapping.

21. An apparatus for detecting at least two receptors in at least one biological sample in a flow stream for at least one of immunoassays, complex genetic analyses, and enzymatic assays, the at least one biological sample including at least two indicators indicating a presence of the at least two receptors upon excitation, said apparatus comprising:
- at least one light source emitting at least two light rays substantially simultaneously toward at least two regions on said at least one biological sample;
- at least one optical detector detecting at least two light rays one of sequentially, simultaneously, and substantially simultaneously, emmitted from the at least two regions on the at least one biological sample via detecting the at least two indicators indicating the presence of the at least two receptors for the at least one of immunoassays, complex genetic analyses, and enzymatic assays.

22. An apparatus for detecting at least two receptors in at least one biological sample in a flow stream for at least one of immunoassays, complex genetic analyses, and enzymatic assays, the at least one biological sample including at least two indicators indicating a presence of the at least two receptors upon excitation, said apparatus comprising:
- first means for emitting at least two light rays one of sequentially, simultaneously, and substantially simultaneously, toward a substantially identical region on said at least one biological sample;
- second means for detecting at least two light rays one of sequentially, simultaneously, and substantially simultaneously, emmitted from the substantially identical region on the at least one biological sample via detecting the at least two . indicators indicating the presence of the at least two receptors for the at least one of immunoassays, complex genetic analyses, and enzymatic assays.

* * * * *